United States Patent [19]

Hilderbrand et al.

[11] Patent Number: 5,283,370
[45] Date of Patent: Feb. 1, 1994

[54] PROCESS FOR THE PARTIAL DEHYDRATION OF A CRUDE WATER-WET ORGANIC STREAM OF THE MONOHYDROPEROXIDE OF P-DIISOPROPYLBENZENE

[76] Inventors: J. Ronald Hilderbrand, 507 Red Oak La., Kingsport, Tenn. 37663; Stephan B. Meydell, III, 3013 West Parkridge Ave., Appleton, Wis. 54914

[21] Appl. No.: 998,980
[22] Filed: Dec. 31, 1992
[51] Int. Cl.$^5$ .......................................... C07C 409/00
[52] U.S. Cl. ..................................... 568/576; 568/562
[58] Field of Search ............................. 568/562, 576

[56] References Cited

U.S. PATENT DOCUMENTS 3,190,924 6/1965 Sodomann ........................ 568/562

FOREIGN PATENT DOCUMENTS 2-15468 9/1991 Japan ................................. 568/576

OTHER PUBLICATIONS

"Solvent Dehydration by Salting Out" in Industrial and Engineering Chemistry, vol. 36, No. 9, pp. 816–820.
"Solvent Dehydration by Salting Out" in Industrial and Engineering Chemistry, vol. 36, No. 10, pp. 917–921.
"Society of Automotive Engineers" May 10–13, (1971), No. 710440, pp. 1–8.
"Liquid/Liquid and Gas/Liquid Coalescing Handbook", Osmonics, pp. 8–10.
"Encyclopedia of Chemical Technology", vol. 13, published by Wiley-Interscience, pp. 49–50.

Primary Examiner—Werren B. Lone
Attorney, Agent, or Firm—Mark A. Montgomery; William P. Heath, Jr.

[57] ABSTRACT

A process for the partial dehydration and partial purification of a crude water-wet organic stream of the monohydroperoxide of p-diisopropylbenzene is disclosed. This crude stream of monohydroperoxide contains at least 2 wt % water and is partially dehydrated by contacting the stream with a non-reactive inorganic salt to remove a portion of the water into a concentrated brine of the inorganic salt followed by separation of the concentrated brine and the product. The crude water-wet organic stream of the monohydroperoxide is optionally filtered and coalesced prior to contacting the nonreactive inorganic salt.

17 Claims, 1 Drawing Sheet

PROCESS FOR THE PARTIAL DEHYDRATION OF A CRUDE WATER-WET ORGANIC STREAM OF THE MONOHYDROPEROXIDE OF P-DIISOPROPYLBENZENE

FIELD OF THE INVENTION

The present invention relates to the removal of water from a crude water-wet stream of the monohydroperoxide of p-diisopropylbenzene. More particularly the present invention relates to the dehydration of a water-wet stream of monohydroperoxide using an inorganic salt.

BACKGROUND OF THE INVENTION

Hydroperoxides are useful for many applications in industry such as in the SBR rubber industry to initiate the polymerization of rubber. A purge stream of hydroperoxide is produced during the production of hydroquinone from p-diisopropylbenzene (DIPB) using air oxidation. This purge stream of hydroperoxides is a waste stream containing many compounds and contaminants and is presently disposed of by incineration.

During production of hydroquinone from DIPB using air oxidation, the monohydroperoxide of p-diisopropylbenzene (MHP) is produced and re circulated until it forms the dihydroperoxide of p-diisopropylbenzene (DHP). The DHP is extracted from the loop in a mixer/settler using weak caustic. The organic phase overflows from the mixer/settler and is recycled back to the oxidizers and thus contains dispersed and dissolved water. During this oxidation reaction, unwanted carbinols and other impurities are produced which must be purged. The purge stream is taken from the MHP loop and is presently cleaved with acid and burned in an incinerator. This purge stream is a crude water-wet organic stream of MHP and is composed of about 50% MHP, 25% DIPB, the remainder being dissolved and dispersed water, carbinols, other unwanted hydroperoxides, and dispersed solids. This crude water-wet organic stream of MHP is saturated with water at 55° C. and contains greater than 2 wt % water and is cloudy in appearance. This crude water-wet organic stream of MHP is not suitable as a feed for any useful reaction since it contains impurities and is a heterogenous mixture that separates into two liquid phases over time. However, if the purity of this stream could be dramatically improved, it would be useful for example as a polymerization initiator for the rubber industry.

It would be very desirable to produce a more pure homogeneous phase from the crude water-wet organic stream of MHP to be useful as a feed for industry such as a polymerization initiator for the rubber industry.

This crude water-wet organic stream of MHP could be purified by distillation or dehydrated by vacuum stripping. However, the temperature required for distillation and/or vacuum stripping exceeds 70° C. and the initiation of a runaway reaction commences at 90° C. Therefore, the distillation or vacuum stripping of this crude water-wet organic stream of MHP is very dangerous even under vacuum since a loss of vacuum could suddenly raise the temperature and start a runaway reaction resulting in an explosion.

Attempts at freezing the dispersed/dissolved water followed by filtration is not possible due to the extremely high viscosity of the chilled stream which consists mostly of MHP.

Attempts were also made at removing the dispersed water simply by coalescing the crude water-wet organic stream of MHP, however, the resulting product from this coalescence forms two phases after a freeze/thaw cycle and is unacceptable for use in feed streams.

The use of drying agents such as silica gel, molecular sieves, or other hydroscopic materials to purify and remove all the water from the stream is not possible since these agents or materials must, due to the economics, be regenerated by heating to remove the extracted water. This is unacceptable for safety reasons since the MHP adhering to the drying agents would cause a runaway reaction during regeneration.

It would be very desirable to be able to economically and safely purify the crude water-wet organic stream of MHP avoiding the above problems.

SUMMARY OF THE INVENTION

The process according to the present invention for the partial dehydration and partial purification of a crude water-wet organic stream of the monohydroperoxide of p-diisopropylbenzene containing at least 2 wt % water comprises:

(a) contacting said stream containing said monohydroperoxide with a non reactive inorganic salt to remove at least a portion of the water into a concentrated brine of said inorganic salt to form a product that contains less than the 10° C. saturation amount of water; and (b) separating said concentrated brine and said product, wherein the product has also been filtered to remove dispersed solid particles to form a clear product.

According to another feature of the present invention the organic stream of the monohydroperoxide of p-diisopropylbenzene is partially dehydrated by being passed through a column that is packed with said nonreactive inorganic salt in particulate form.

DETAILED DESCRIPTION OF THE INVENTION

Figure 1:
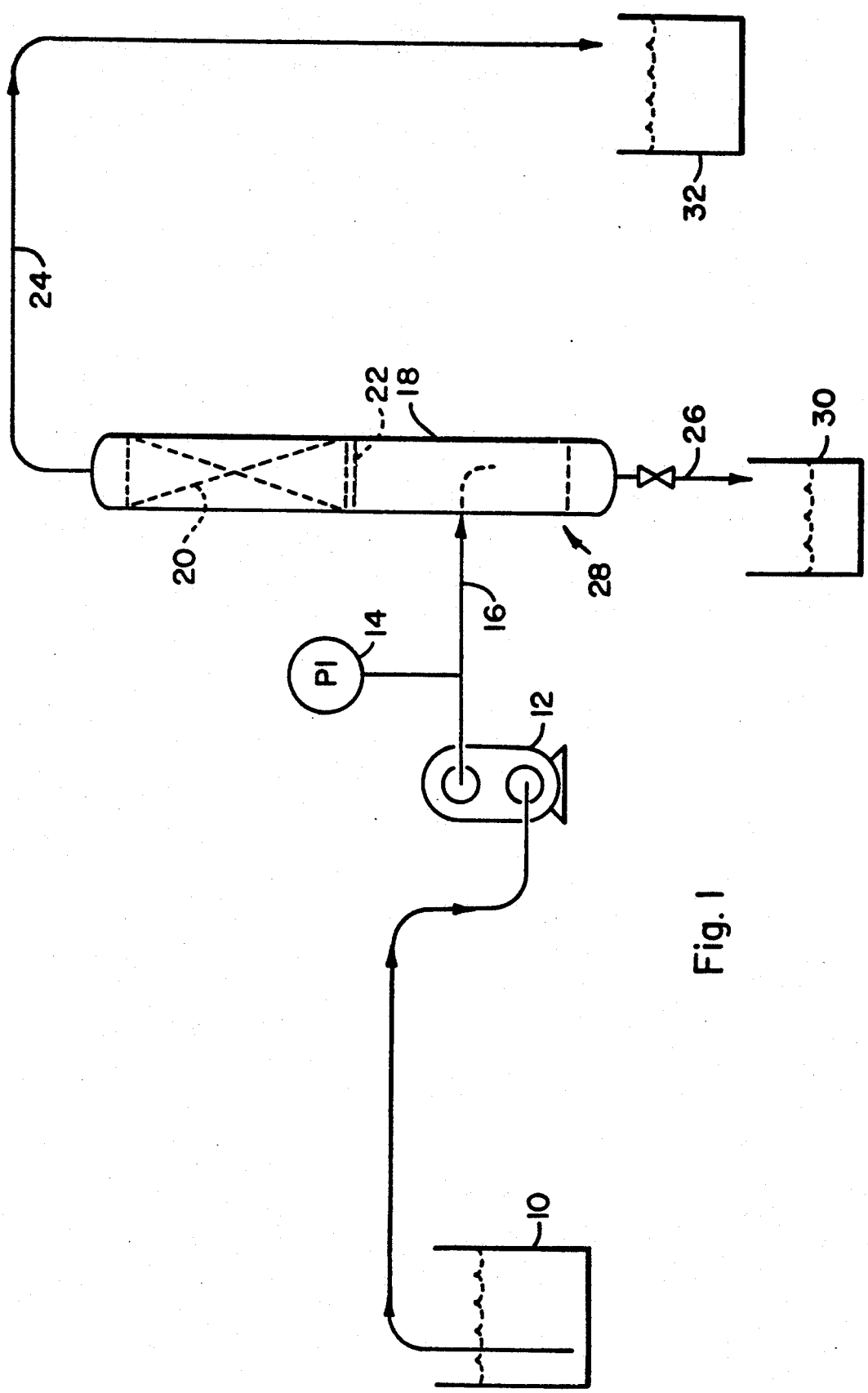
FIG. 1 This figure illustrates a preferred method of the partial dehydration of the crude water-wet organic stream of the MHP.

The applicants have unexpectedly discovered an improved method of forming a useful product by the partial dehydration and partial purification of a crude water-wet organic stream of MHP that initially contains at least 2 wt % water. Applicants unexpectedly discovered that this stream could be partially dehydrated and partially purified by the use of a nonreactive inorganic salt. Applicants also unexpectedly discovered that this stream can be made into a useful product by only partially dehydrating the stream to below 2 wt % particularly below 1.7% water. At this low concentration of water, repeated freeze/thaw cycles does not cause phase separation.

A more preferred process for the partial dehydration and partial purification of the crude water-wet organic stream of MHP containing at least 2 wt % water comprises filtering the organic stream to remove dispersed solid particles; coalescing the filtered stream to remove at least a portion of the dispersed water; separating the coalesced water and organic stream by decantation; passing the decanted organic stream through a column packed with a non reactive inorganic salt in particulate form to remove at least a portion of the water into a concentrated brine of said inorganic salt to form a clear product that contains less than the 10° C. saturation amount of water; and separating said concentrated brine and said product.

This preferred method is particularly illustrated in FIG. 1. The filtered, coalesced, and decanted crude water-wet organic stream of MHP 10 is pumped at 25° C. through a metering pump 12 monitored by a pressure gauge 14 through line 16 into a column 18. This crude organic stream of MHP passes up in the column 10 through a support plate 22 (such as a fritted glass support plate) through a packed column of particulate salt out through line 24 and collected 32. The brine formed in the salt bed 20 flows countercurrent to the organic stream through the support plate 22 down through the feed section to the organic stream/brine interface 28 down through line 26 and collected 30.

The crude water-wet organic stream of MHP is preferrably coalesced prior to contacting the nonreactive inorganic salt to remove at least a portion of the dispersed water. The coalescing of at least a portion up to all of the dispersed water requires less salt contact time to remove the required portion of the dissolved water in the crude stream of MHP. The coalescing is preferably conducted by passing the MHP stream through a depth type coalescing element such as OSMO LS180P manufactured by OSMONICS, INC., allowing the phases to separate and decanting the water thereby removing essentially all of the dispersed water in the crude stream of MHP. Depth type coalescing elements are disclosed in "Liquid/Liquid and Gas/Liquid Coalescing Handbook" pages 8-10, published by OSMONICS, INC., in 1989/1991.

The applicants have also unexpectedly discovered that the crude stream of MHP must be filtered at some point during the dehydration/purification process to produce a feed that is acceptable and clear. This filtration step is preferably conducted prior to contacting the inorganic salt and prior to the coalescing process. Filtration starts the coalescence process. Filtration is preferably conducted through an absolute filter to remove at least the 2 micron size dispersed particles.

The crude stream of MHP must not be too viscous otherwise the filtration and coalescence would not be possible, thus the temperature of the crude stream of MHP must be at least 10° C. Additionally, the crude stream of MHP should, for safety reasons, not be higher than 85° C. since at 90° C. the crude stream of MHP will decompose by a runaway reaction. During the partial dehydration and partial purification of the crude stream of MHP, the temperature of this stream is preferably between 20° C. and 30° C. with a temperature of about room temperature due to ease of handling being most preferred.

It is preferred that the crude stream of MHP be initially contacted with the non reactive inorganic salt in particulate form causing the concentrated brine to be formed by extraction of the water from the crude stream of MHP. This contacting of the crude stream of MHP with the particulate inorganic salt is more preferably conducted by passing the crude stream of MHP through a column packed with the salt in particulate form as discussed above. The crude stream of MHP can be passed through the column in a downflow or upflow mode. However, upflow is preferred due to the tendency of the heavier brine to settle in the bottom of the column and to prevent channeling which occurs in the downflow mode. The residence time of the crude stream of MHP in the packed column of particulate salt generally depends on the average particle size of the particulate salt. The residence time of the crude stream of MHP in a packed column having salt particles with an average particle size of less than 3 cm in diameter is generally less than 6 hours. The residence time required can be reduced by reducing the particle size of the salt which exposes more surface area. Using a salt with an average particle size of approximately 1000 microns results in a required residence time of about 10 minutes.

The chemical composition of the non reactive inorganic salt can vary somewhat, however, it is preferred that the salt form a brine without producing a large exothermic heat of solution and/or heat of hydration. The non reactive inorganic salt is generally selected from the group of salts consisting of alkali metal and alkaline earth metal salts of chlorine, sulfur and nitrogen. However, due to ease in handling and safety reasons, the alkali metal chlorides are more preferred with sodium chloride being the most preferred due to economics.

The crude water-wet organic stream of MHP generally contains at least 3.5 wt % dispersed and dissolved water whereas the partially dehydrated and partially purified stream contains less than 2 wt % water, preferably less than 1.7 wt % with less than 1.6 wt % being most preferred. The crude water-wet stream of MHP contains about 2 to 3 wt % dissolved water. The crude water-wet stream of MHP need not be totally dehydrated to be useful as a feed stream thus a water content of greater than 1% up to about 1.7% is generally preferred. Removing water down to below 1 wt % is not required and would generally not be economically practical. The amount of water present in the final MHP product generally needs to be the amount that does not form a separate phase after a freeze/thaw cycle. This amount is generally below 1.7 wt % and is less than the 10° C. saturation amount of water. However, it is preferred that the product contain less than the 0° C. saturation amount of water with a content of less than the $-10°$ C. saturation amount of water being most preferred.

When using the salt column in the partial dehydration and partial purification of the crude water-wet stream of MHP, the salt column is refilled from time to time with particulate salt depending upon the inlet water concentration and the flowrate. For a nominal gpm flow of the crude water-wet stream of MHP at 3.0% water, salt will be added about once per month.

The following examples are intended to illustrate the present invention without being a limitation on the reasonable scope thereof.

EXAMPLES

EXAMPLE 1

A 1 inch diameter glass column was filled with 20 inches of reagent grade, sodium chloride. A total of 322 grams of salt was used. A glass frit support plate was installed just above the side take off to support the salt and prevent it from clogging either the side or the bottom outlet in the downflow column. The side takeoff outlet extended into the column and was turned down opposite the direction of flow to eliminate the possibility of brine leaving the column in the product stream.

The side take off was attached to another 1 inch diameter glass column of the same height. This column was designed to fill with the partially dehydrated monohydroperoxide to ensure that the salt column voids were filled with liquid. Also, any air bubbles forced into the product column would disengage from the brine to ensure that the product flowing out of the top of the product column was free of dispersed brine.

A five gallon sample of a crude water-wet stream of the monohydroperoxide of DIPB was obtained from a hydroquinone plant that uses the DIPB oxidation process as described in Kirk Othmer, *Encyclopedia of Chemical Technology*, Third Edition, Volume 13, pages 49 and 50, John Wiley and Sons, Inc., 1981. This stream was allowed to cool to 25° C. The crude water-wet monohydroperoxide contained about 50 wt. % monohydroperoxide, 25 wt. % p-diisopropylbenzene, the remainder being carbinols, other hydroperoxides, dispersed solids, and water. The crude monohydroperoxide containing emulsified water was first filtered through a 0.4 micron fiber glass filter to remove the dispersed solids and start the coalescing process which removes some water. The crude unfiltered monohydroperoxide analyzed 2.59% water while the filtered material analyzed 2.16% water. The coalesced water was removed by decantation.

The filtered monohydroperoxide was pumped at a rate of 10 milliliters per minute down through the salt column for 5 hours. During this time period, brine was seen separating from the organic phase and accumulating in the bottom of the salt column. After 4 hours of running, 10.5 grams of brine was removed from the salt column using the bottom outlet valve. This waste brine stream was analyzed and found to contain 0.11% of the monohydroperoxide and less than 0.1% DIPB.

Once the product column was filled, which required approximately 1 hour, stream samples were taken and analyzed for percent water using a Carl Fisher apparatus similar to ASTM E203 and for turbidity according to the following procedure in which the sample is loaded into an 8 dram vial and inserted into a HACH RATIO TURBIDIMETER. Visible light is passed through the sample, and the transmittance is measured and compared to a standard. Deionized water typically analyzed 0.1 NTU whereas the crude unfiltered oxidate (crude stream of MHP) typically analyzed about 100 NTU. The results are illustrated below in Table 1.

TABLE 1

| TIME (HOURS) | % WATER | TURBIDITY (NTU) |
|---|---|---|
| 0 | 1.57 | 0.18 |
| 1 | 1.64 | — |
| 3 | 1.57 | 0.19 |
| 5 | 1.59 | 0.24 |

The residence time or contact time of the monohydroperoxide with the salt was calculated at 10.8 minutes. The pressure on the column was initially measured at 6.0 psig, and it rose to 6.5 psig at the end of the 5 hour run. The product in all of the samples from 0 to 5 hours was haze free (<1 NTU) and did not separate into 2 phases after repeated freeze thaw cycles. It was determined that soluble water levels at or below 1.7% water in the partially dehydrated monohydroperoxide will not separate after repeated freeze/thaw cycles (−10° C. to +30° C.).

EXAMPLE 2

In this example, all conditions were the same as Example 1 except that the crude monohydroperoxide flow rate was increased from 10 ml/minute to 20 ml/minute which reduced the residence time to 5.4 minutes. The pressure across the salt column was 14 psig, and the run was maintained for 30 minutes after which a stream sample was analyzed. Water was 1.50% and turbidity was 0.72 NTU. This sample was haze free.

EXAMPLE 3

In this example, all conditions were the same as Example 1 except that crude unfiltered monohydroperoxide was fed into the salt column at 10 ml/minute. The column was operated for 2 hours before the stream sample was taken. The sample analyzed 1.4% water, but the turbidity was 2.5 NTU. This sample was acceptable for percent water, but the haze was unacceptable due to appearance. This experiment demonstrated that the salt column could remove water down to the equilibrium level but could not remove the insoluble particulates.

EXAMPLE 4

In this example, all conditions were the same as Example 1 except the filtered monohydroperoxide was fed at 5 ml/minute for a residence time of 21.6 minutes. The pressure drop across the salt column was measured at the start of the run at 3.4 psig and increased to 4.4 psig during the 2.5 hour run. The product stream sample analyzed 1.63% water, and turbidity was 0.85 NTU. The starting material that had been filtered and decanted was 2.16% water, and the turbidity was 10.4 NTU.

EXAMPLE 5

This example was conducted similar to Example 1 except that a ⅜ inch diameter column filled with 22 inches of calcium chloride salt was used. Filtered, and decanted crude water-wet monohydroperoxide analyzing 2.03% water and 1.4 NTU turbidity was fed at 25° C. at rate of 6 ml/minute for a calculated residence time of 10 minutes. The product sample analyzed 1.09% water and 0.27 NTU turbidity after a run time of one hour.

EXAMPLE 6

In this example the column diameter and length were increased to 2 inches and 27 inches respectively and the crude filtered monohydroperoxide flowrate was decreased to 2.3 ml per minute. The contact time was increased to approximately 4 hours which was necessary since the salt used was changed from reagent grade granular to compacted, AKZO Brand water softener grade PD 5700 which has much less surface area per unit volume than the salt used in Examples 1–5. The new column was fed from the bottom and the monohydroperoxide flowed upward through the salt bed as illustrated in FIG. 1. Brine formed in the bed and flowed down through the salt counter to the flowing monohydroperoxide. At the bottom of the column, the brine formed a separate layer and was periodically drained. The column was charged with 1130 grams of salt and fed for 150 hours continuously. The temperature of the monohydroperoxide was 25° C. A composite 5 gallon sample of the product leaving the column analyzed 1.44% water and turbidity was 0.10 NTU. The feed for this example was obtained from the same operating hydroquinone plant as Example 1 and was filtered and coalesced prior to its use, and contained 2.10% water.

EXAMPLE 7: (Comparative)

Crude, filtered monohydroperoxide, from the same operating hydroquinone plant as Example 1, was pumped at 25° C. through a coalescing element at 10 ml/min. The element coalesced the dispersed water and 2 phases were formed. The top organic phase was decanted and analyzed 2.1% water. The sample was subjected to freeze/thaw conditions and a haze was formed after the first cycle. The haze proved that a second insoluble water phase was formed and persisted at room temperature which was unacceptable. The monohydroperoxide was filtered at room temperature through a 0.4 micron filter but this was unsuccessful in removing the haze. At 10° C. or less the viscosity of the monohydroperoxide makes filtration very difficult and still does not remove the haze.

We claim:

1. A process for the partial dehydration and partial purification of a crude water-wet organic stream of the monohydroperoxide of p-diisopropylbenzene containing at least 2 wt % water comprising:
   (a) contacting said stream containing said monohydroperoxide with a non reactive inorganic salt to remove at least a portion of the water into a concentrated brine of said inorganic salt to form a product that contains less than the 10° C. saturation amount of water; and
   (b) separating said concentrated brine and said product,
   wherein the product has also been filtered to remove dispersed solid particles to form a clear product.

2. The process according to claim 1 further comprising filtering, coalescing, and settling said stream to remove said dispersed solid particles and part of the dispersed water prior to step (a).

3. The process according to claim 2 wherein said stream is only partially coalesced by passing said stream through a depth type coalescing element, allowing the phases to separate, and decanting the water to remove essentially all of the dispersed water.

4. The process according to claim 3 wherein said stream is at a temperature between 10° and 85° C.

5. The process according to claim 1 wherein said inorganic salt is initially in particulate form when contacted with said stream.

6. The process according to claim 5 wherein step (a) is conducted by passing said stream through a column packed with said salt in particulate form.

7. The process according to claim 6 wherein said stream is passed up through said column.

8. The process according to claim 6 wherein the residence time of said stream in said column is less than 6 hours and the average particle size of said salt in particulate form is less than 3 cm in diameter.

9. The process according to claim 1 wherein said salt is a salt that forms a brine without producing a large exothermic heat of solution or hydration.

10. The process according to claim 1 wherein said salt is selected from the group consisting of the alkali metal and alkaline earth metal salts of chlorine, sulfur, and nitrogen.

11. The process according to claim 10 wherein said salt is an alkali metal chloride.

12. The process according to claim 11 wherein said salt is sodium chloride.

13. The process according to claim 1 wherein said crude water-wet organic stream contains at least 3.0 wt % water.

14. The process according to claim 1 wherein said product contains less than 2 wt % water.

15. The process according to claim 14 wherein said product contains about 1 to 1.7 wt % water.

16. The process according to claim 1 wherein said product contains less than the −10° C. saturation amount of water.

17. The process according to claim 1 wherein said partially dehydrated product has a turbidity of less than 1 NTU.

* * * * *